United States Patent [19]
Ohnishi et al.

[11] Patent Number: 5,641,432
[45] Date of Patent: Jun. 24, 1997

[54] DICYCLOHEXYLETHYLENE DERIVATIVE

[75] Inventors: Noriyuki Ohnishi, Kumamoto; Shuichi Matsui, Chiba; Tomoyuki Kondo, Chiba; Yasuyuki Goto, Chiba, all of Japan

[73] Assignee: Chisso Corporation, Osaka, Japan

[21] Appl. No.: 522,322

[22] PCT Filed: Mar. 10, 1994

[86] PCT No.: PCT/JP94/00389

§ 371 Date: Oct. 26, 1995

§ 102(e) Date: Oct. 26, 1995

[87] PCT Pub. No.: WO94/20443

PCT Pub. Date: Sep. 15, 1994

[30] Foreign Application Priority Data

Mar. 10, 1993 [JP] Japan .................. 5-077551

[51] Int. Cl.[6] ................. C09K 19/30; C07C 19/08
[52] U.S. Cl. ................. 252/299.63; 570/128
[58] Field of Search ................. 252/299.63; 570/128

[56] References Cited

U.S. PATENT DOCUMENTS

| | | | |
|---|---|---|---|
| 4,853,152 | 8/1989 | Goto et al. | 252/299.63 |
| 5,032,313 | 7/1991 | Goto et al. | 252/299.63 |
| 5,055,220 | 10/1991 | Uchida et al. | 252/299.01 |
| 5,308,541 | 5/1994 | Hittich et al. | 252/299.63 |
| 5,358,662 | 10/1994 | Hirose et al. | 252/299.63 |

*Primary Examiner*—C. H. Kelly
*Attorney, Agent, or Firm*—Wenderoth, Lind & Ponack

[57] ABSTRACT

As a liquid crystal compound, a dicyclohexylethylene derivative, which has a wide liquid crystal phase temperature range, a low viscosity, a large $\Delta\epsilon$ value, a high stability, and an excellent compatibility with other liquid crystal compounds. The dicyclohexylethylene derivative is represented by general formula (I),

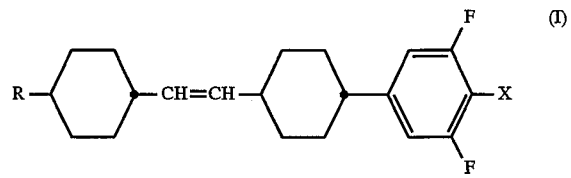

wherein R represents $C_1$–$C_{10}$ linear alkyl; and X represents fluorine or trifluoromethyl. This compound can widen the working range of a liquid crystal display element because of its high NI point, can improve the response speed of the display element because of its low viscosity, and can lower the voltage for driving the display element because of its high positive $\Delta\epsilon$ value. Furthermore, it is so stable against changes in environmental factors that it can be used in various liquid crystal display elements of, for example, active matrix drive type using TFT.

4 Claims, No Drawings

DICYCLOHEXYLETHYLENE DERIVATIVE

TECHNICAL FIELD

This invention relates to a dicyclohexylethylene derivative. More particularly, it relates to a dicyclohexylethylene derivative which is a compound preferred as a component of display materials, and to a liquid crystal composition containing the derivative.

BACKGROUND ART

In recent years, liquid crystal display elements have been introduced into personal computers and OA apparatus, as display devices, and the importance thereof has been rapidly increasing. For the computers and apparatus, display devices of such a mode as supertwisted nematic (STN) or supertwisted birefringence effect (SBE), and active matrix using a thin film transistor (TFT), among various modes of liquid crystal display have been employed.

The reason is that the quantities of information have been increased by employing these modes, and as a result, color display and magnification of picture of display have become possible. For the liquid crystal materials used for these display modes, various characteristics are required, such that the materials have liquid crystal phases within a temperature region where display elements are used; are stable to environmental factors (moisture, heat, air, light, electricity, etc.); are colorless; are large (or small) in the quantity of the anisotropy of refractive index (herein abbreviated to Δn); are large in the quantity of the dielectric anisotropy (hereinafter abbreviated to Δε); are low in the viscosity; are high in the specific resistivity and yet small in its change with lapse of time; and are broad in d/p margin (d: cell thickness and p: pitch length). However, at present, a single compound which satisfies these requirements and thus is usable for display elements is not available. Thus, practically used liquid crystal materials are ones obtained by mixing several kinds of liquid crystalline compounds or by mixing these compounds with other compounds having specific objects. Accordingly, the liquid crystalline compounds should have a good compatibility with other liquid crystals. Liquid crystalline compounds referred to in this specification mean compounds which, even if they do not apparently exhibit mesophases by themselves, contribute to various characteristics as liquid crystals in a certain aspect when they are mixed with liquid crystal substances.

As a compound similar to that of the present invention, a compound expressed by the following formula (II) has been known:

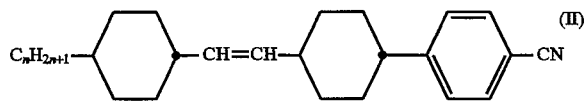

wherein n represents an integer of 3, 4, 5, 6 or 7 (Japanese patent application laid-open No. Sho 61-215336). However, this compound has a high viscosity and an inferior compatibility with a number of already known liquid crystal compounds at low temperatures. Further, this compound has a drawback of being difficultly used from the aspects of specific resistivity required for display materials of TFT mode and its change with lapse of time.

Further, a compound similar to that of the present invention and expressed by the following formula (III) has been disclosed in U.S. Pat. No. 5,055,220:

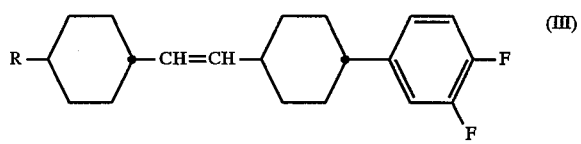

wherein R represents a linear alkyl group of 1 to 8 carbon atoms.

This compound has a broad liquid crystal temperature range and a low viscosity, but it has a weak point of a small dielectric anisotropy.

Still further, fluorine atoms-containing compounds similar to the compound of the present invention, and expressed by the following formulas (IV) and (V) have been disclosed in U.S. Pat. No. 5,032,313 and DE 4,027,840 A1.

Compounds expressed by the formulas (III) and (IV) have a large dielectric anisotropy Δε similarly to the compound of the present invention, but they have a drawback of an inferior solubility in other liquid crystal compounds at low temperatures; hence they are somewhat difficultly used.

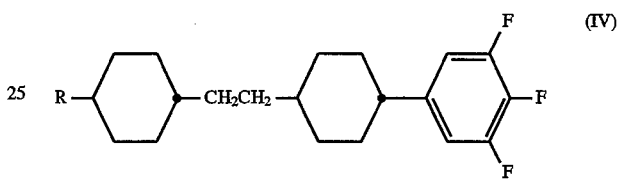

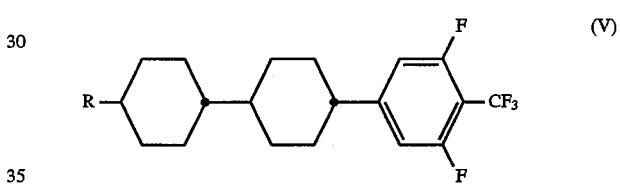

In these formulas, R represents an alkyl group of 1 to 10 carbon atoms.

The compound expressed by the formula (V) is structurally very similar to the compound of the present invention, and the difference between the compounds exists only in that the compound of the present invention has an ethendiyl group as the central bonding group, whereas the compound of the formula (V) has an ethanediyl group as a central bonding group. However, the latter compound has been found to have an induced smectic phase at low temperatures; thus, a drawback that the electro-optical response at low temperatures becomes far inferior is liable to occur. The present inventors have sought a nematic compound which has a dielectric anisotropy of the same extent or more than that of the compound of the formula (V), and does not form any smectic phase at low temperatures when it is mixed with another nematic liquid crystal.

Not only in the liquid crystal display mode mentioned above, but also in various liquid crystal display modes, a broad operation temperature range, a high response speed, and a low driving voltage have been sought.

DISCLOSURE OF THE INVENTION

An object of the present invention is to provide a liquid crystalline compound which has a broad temperature range of liquid crystal phase, a low viscosity, a large Δε, and a high stability, and is excellent in the compatibility with other liquid crystal compounds, while satisfying requirements mentioned above.

The present invention resides in a dicyclohexylethylene derivative expressed by the following formula (I) and a liquid crystal composition containing the derivative as at least one component thereof:

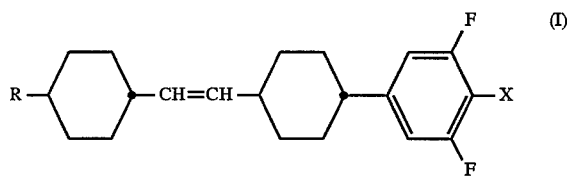
(I)

wherein R represents a linear alkyl group of 1 to 10 carbon atoms; X represents fluorine atom or trifluoromethyl group; both of the 1,4-cyclohexylene groups are of transform; and the ethenediyl group is also of trans-form.

BEST MODE FOR CARRYING OUT THE INVENTION

The compound of the present invention is expressed by the following formulas (Ia) or (Ib), and among them, compounds expressed by the formulas wherein n is 2 to 7 are preferable:

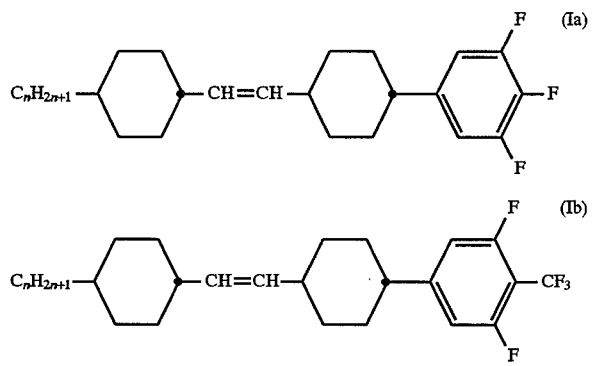

Many of these compounds include a number of compounds exhibiting a broad liquid crystal phase temperature range between from about room temperature up to one hundred and several tens ° C. Since these compounds have an extremely low viscosity and a large $\Delta\epsilon$, for compounds having three six-membered rings, when these compounds are used for liquid crystal materials, it is possible to drive liquid crystal display elements under a low voltage. Further, since the compounds expressed by the above formulas do not exhibit a smectic phase or exhibit a smectic phase within an extremely narrow temperature range, they are preferred as materials for liquid crystal display elements which use a nematic phase.

Further, the compounds expressed by the formula (I) exhibit a superior compatibility with known compounds such as those of ester type, Schiff base type, ethane type, acetylene type, azoxy type, biphenyl type, cyclohexane type, cyclohexene type, pyridine type, pyrimidine type, dioxane type, fluorine type; hence when the compounds of the formula (I) are mixed with these compounds or mixtures thereof, it is possible to prepare liquid crystal materials suitable to various applications.

Further, the compounds of the present invention are very stable to environmental factors (moisture, heat, air, light, electricity, etc.).

Still further, the compounds of the formula (I) are suitable as raw materials for preparing other liquid crystalline compounds. For instance, when they are subjected to catalytic reduction, it is possible to obtain the following liquid crystalline compound expressed by the formula (VI):

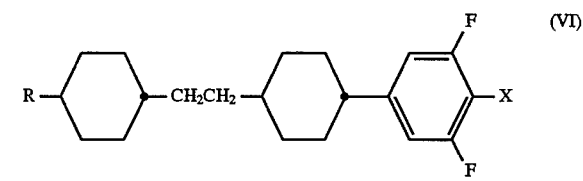
(VI)

A process for preparing the compounds of the present invention is shown below.

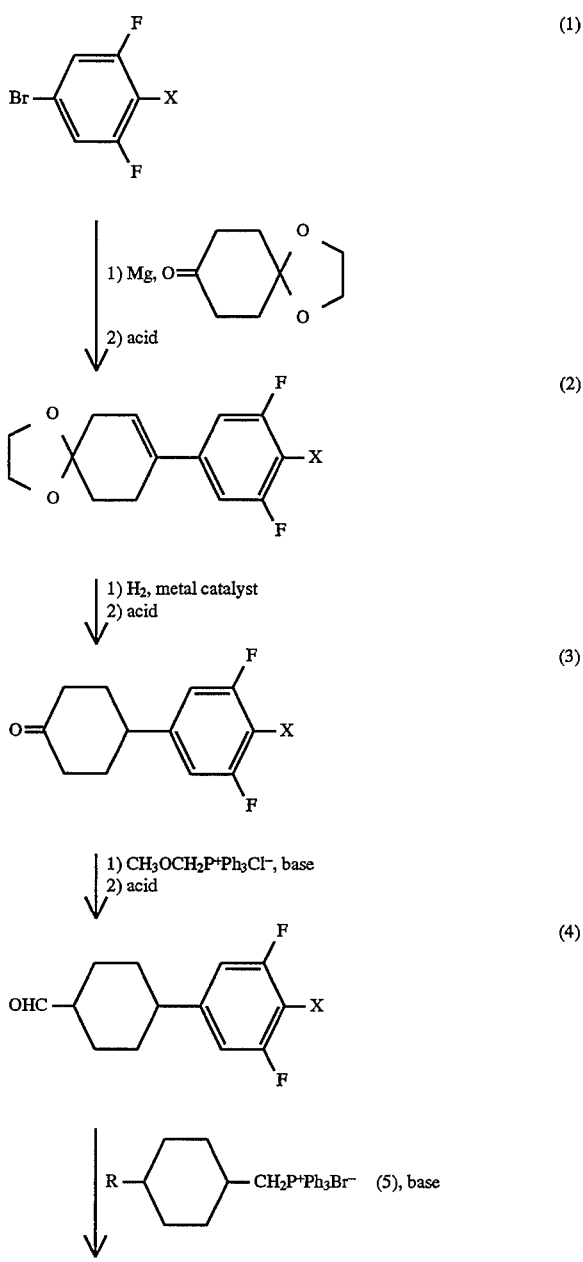

-continued

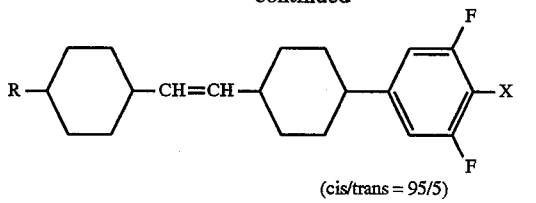

(cis/trans = 95/5)

1) peroxide
2) Ph₃PBr₂
3) Zn

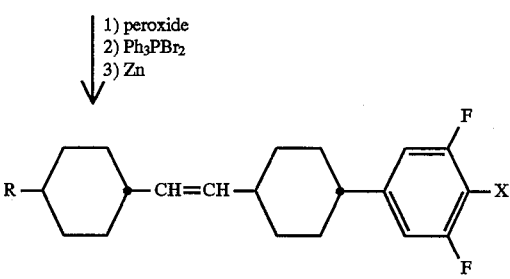

In these formulas, R and X have the same meaning as defined above.

Namely, 1,4-cyclohexanedionemonoethylene ketal is reacted with a Grignard reagent prepared from an arylbromide of the formula (1), followed by carrying out dehydration reaction in the presence of an acid catalyst such as p-toluenesulfonic acid, potassium hydrogen sulfate, hydrochloric acid, sulfuric acid, and a cationic ion-exchange resin to obtain a cyclohexene derivative of the formula (2). After subjecting to catalytic reduction in the presence of a catalyst such as Pd, Ni or Pt system, it was further subjected to a treatment with an acidic aqueous solution to obtain a cyclohexanone derivative of the formula (3). Then an ylide obtained by treating methoxymethyltriphenyl phosphonium chloride with a base such as n-butyl lithium and potassium-t-butoxide is subjected to a reaction with the compound of the formula (3), and further treated in an acidic aqueous solution to obtain an aldehyde derivative of the formula (4). This derivative is reacted with an ylide obtained by treating the phosphonium salt of the formula (5) with a base such as n-butyl lithium and potassium-t-butoxide to obtain a dicyclohexylethylene derivative of the formula (I'). The compound of the formula (I') is a mixture of cis-form substance with trans-form substance, and its ratio is about cis:trans= 95:5. When the cis-form substance is converted into a trans-form substance, the compound of the formula (I) of the present invention is obtained. Namely, an ethylene derivative of the formula (I') is oxidized with a peroxide such as m-chloroperbenzoic acid, followed by brominating with dibromotriphenylphosphorane and finally reducing with Zn, whereby a dicyclohexylethylene derivative of the formula (I) which is a compound of the present invention is obtained.

The liquid crystal composition of the present invention is characterized in that the composition is a liquid crystal composition containing at least two liquid crystalline compounds at least one of which is a liquid crystalline compound expressed by the formula (I) mentioned above.

As other components of the liquid crystal composition of the present invention, at least one component selected from (i) a component (B) containing at least one compound of a high dielectric anisotropy of $\Delta\epsilon \geq 5$, (ii) a component (C) containing at least one compound of a low dielectric anisotropy of $|\Delta\epsilon| < 5$, and (iii) a component (D) containing at least one compound having a clearing point exceeding 80° C., can be mentioned.

The liquid crystal composition provided by the present invention is preferably a liquid crystal dielectric containing two or more components selected from the components (i), (ii) and (iii) and another component (E) in addition to the component (A) containing at least one compound expressed by the formula (I).

Preferable compounds as the component (B) of the liquid crystal composition of the present invention are mentioned below:

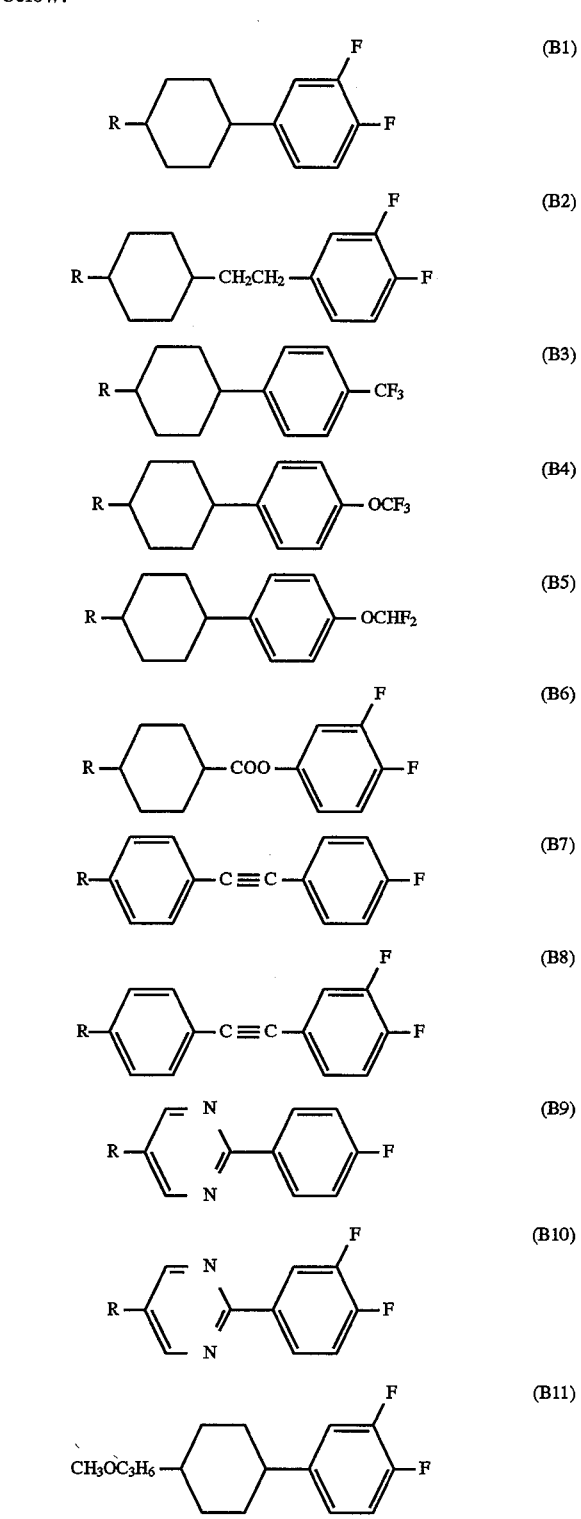

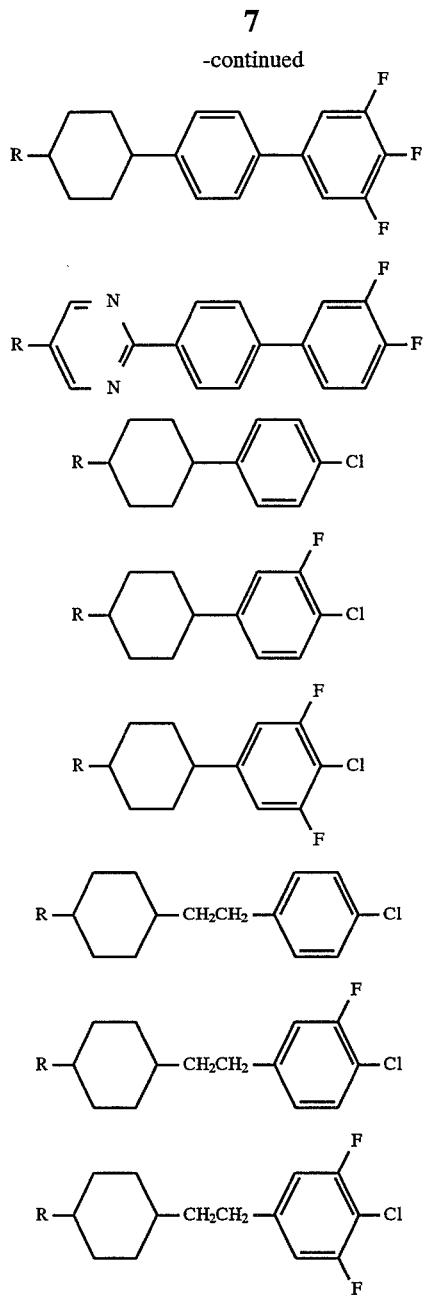
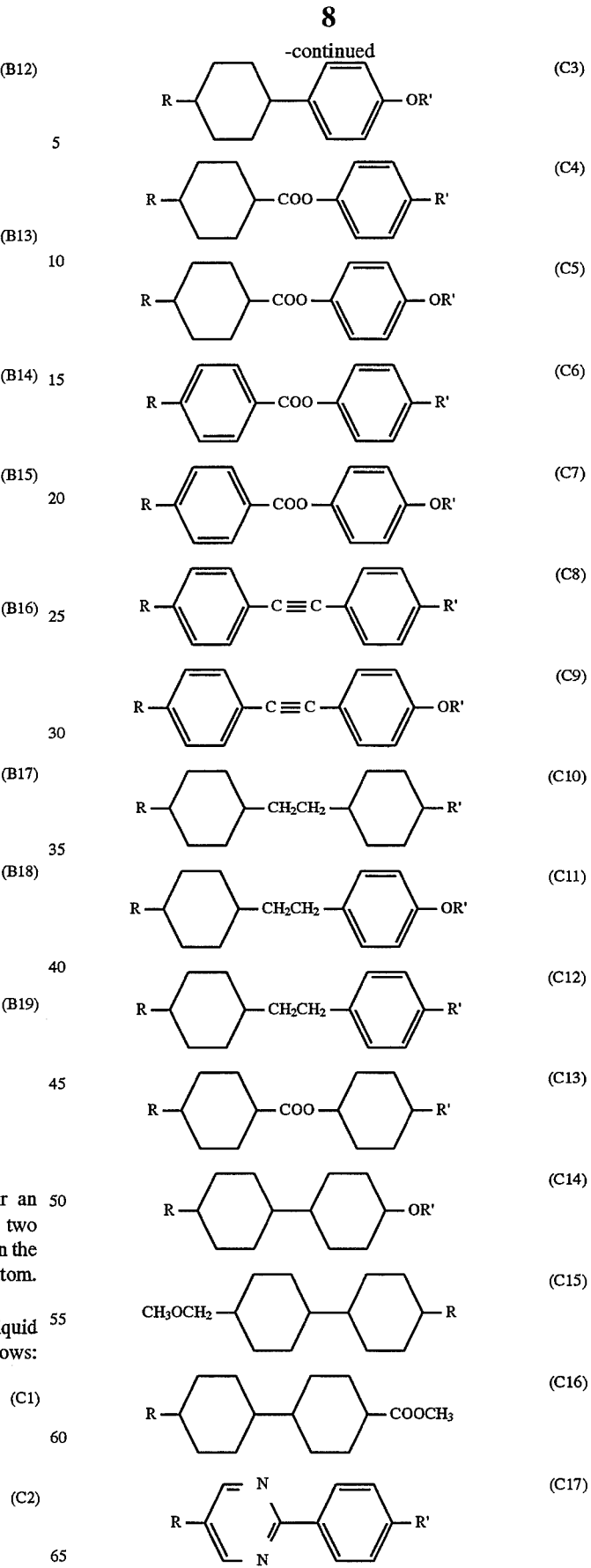
In these formulas, R represents an alkyl group or an alkenyl group of 1 to 10 carbon atoms, and one or two methylene groups which are not adjacent to each other in the groups mentioned above may be replaced by oxygen atom.
Preferable compounds as the component (C) of the liquid crystal composition of the present invention are as follows:
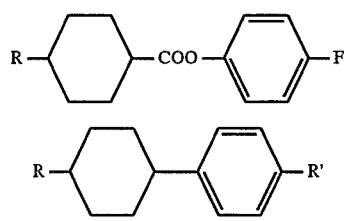

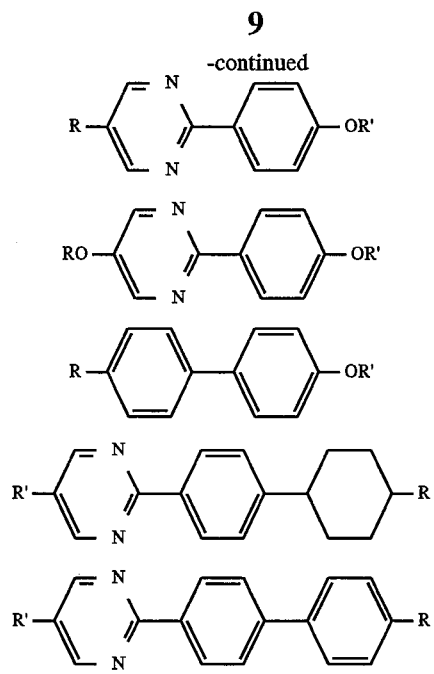
In these formulas, each of R and R' independently represents an alkyl group or an alkenyl group of 1 to 10 carbon atoms, and one or two methylene groups which are not adjacent to each other in the group mentioned above may be replaced by oxygen atom.
Preferable compounds as the component (D) of the liquid crystal composition of the present invention are as follows:
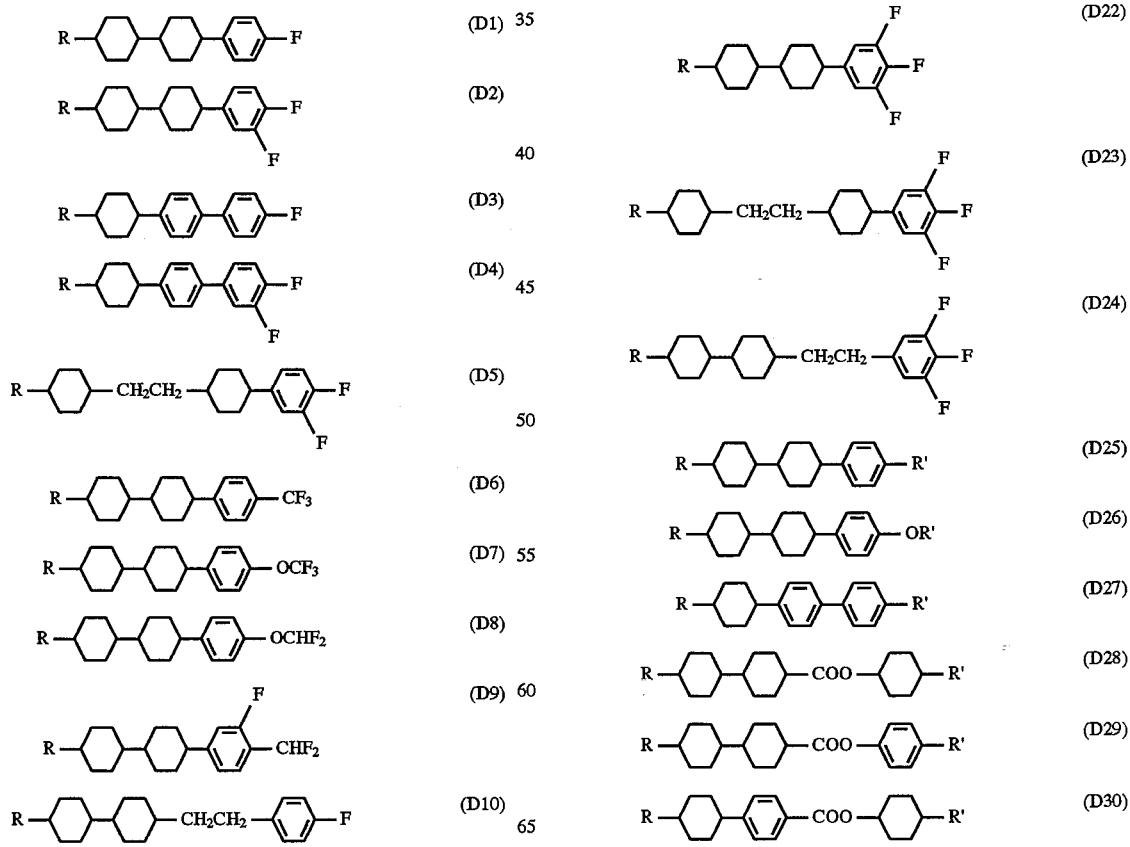

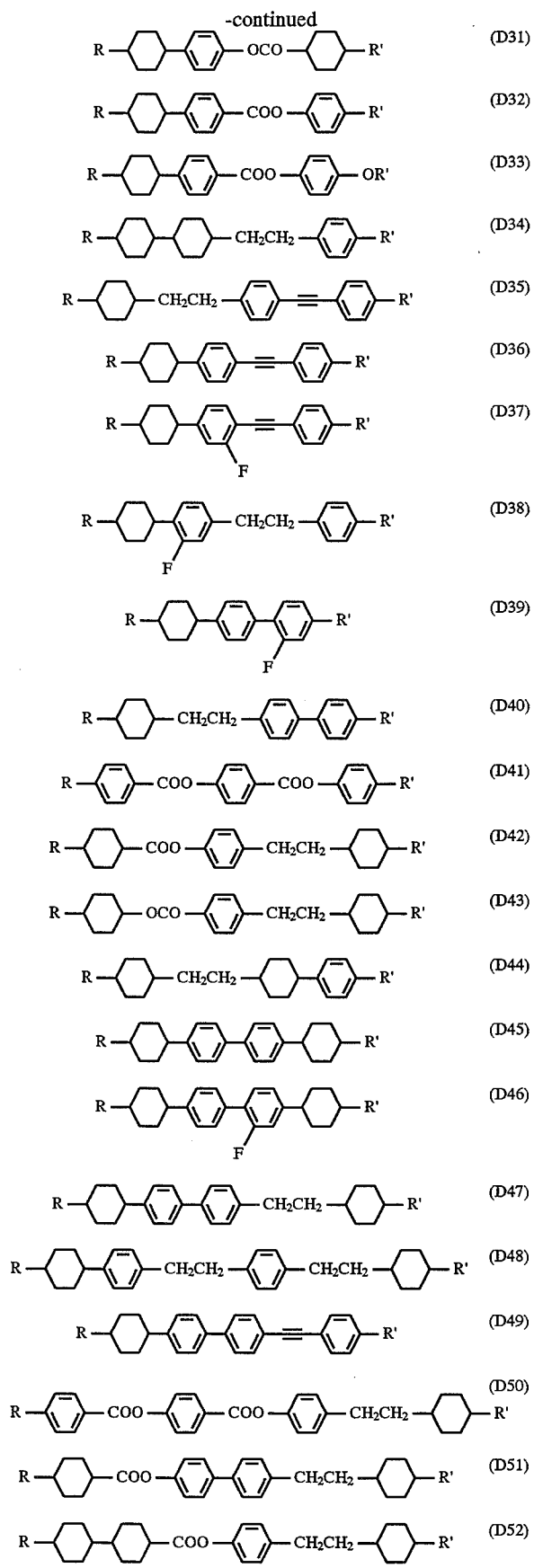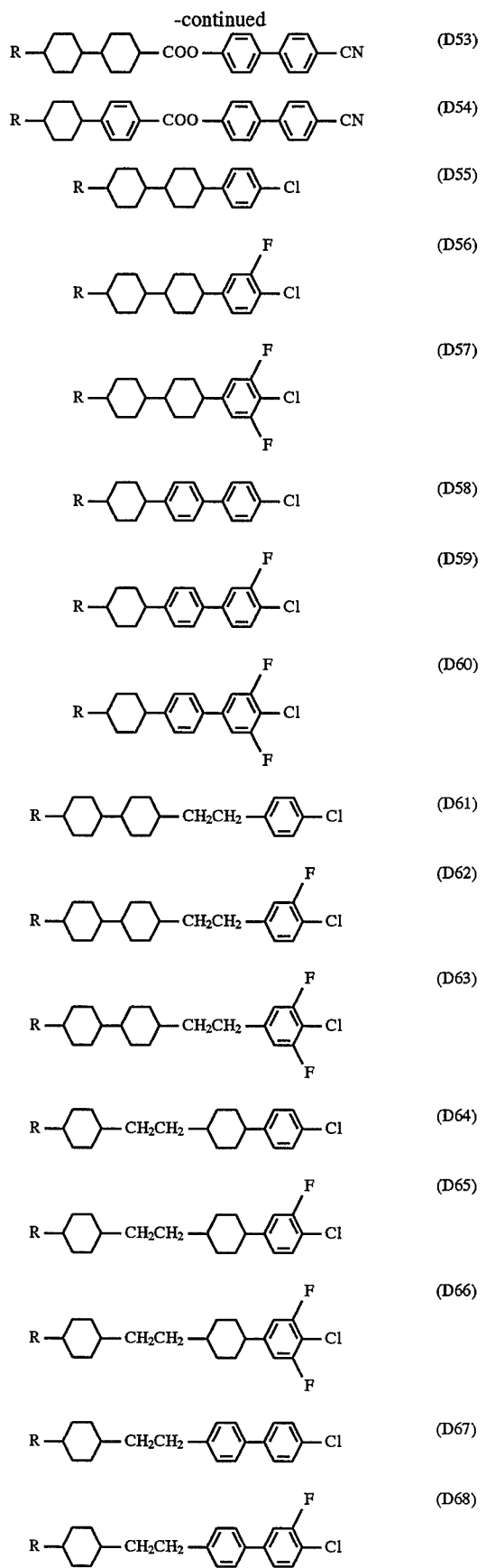

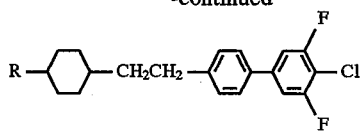
(D69)

In these formulas, each of R and R' independently represents an alkyl group or an alkenyl group of 1 to 10 carbon atoms, and one or two methylene groups which are not adjacent to each other in the group may be replaced by oxygen atom.

Preferable compounds as another component (E) in the liquid crystal composition of the present invention are as follows:

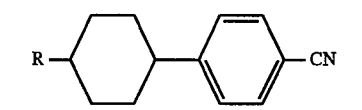
(E1)

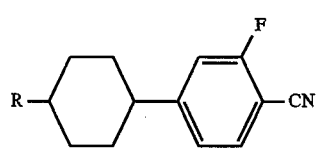
(E2)

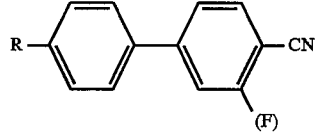
(E3)

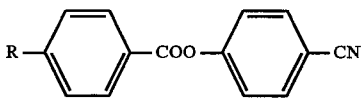
(E4)

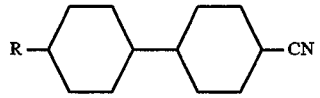
(E5)

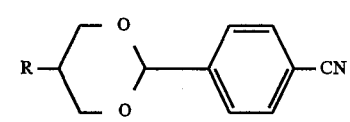
(E6)

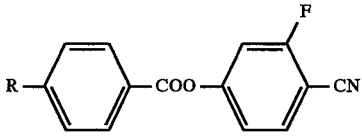
(E7)

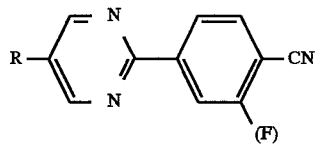
(E8)

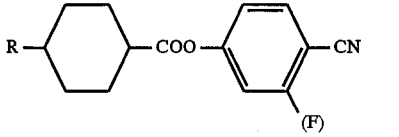
(E9)

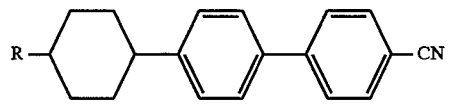
(E10)

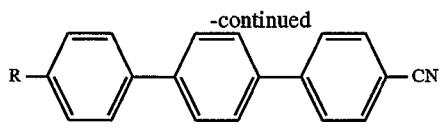
(E11)

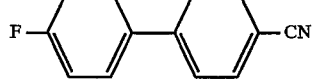
(E12)

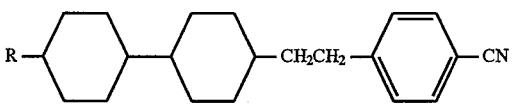
(E13)

(E14)

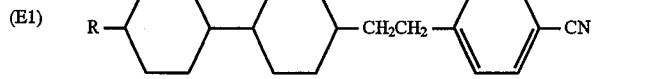
(E15)

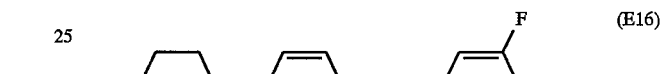
(E16)

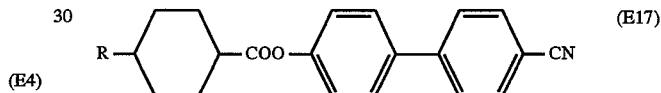
(E17)

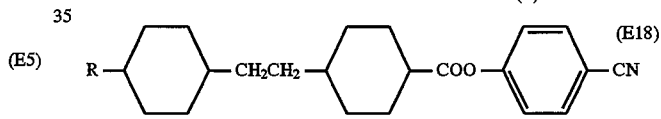
(E18)

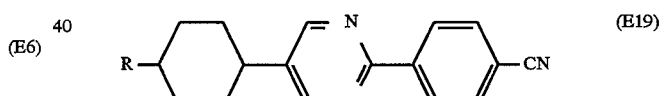
(E19)

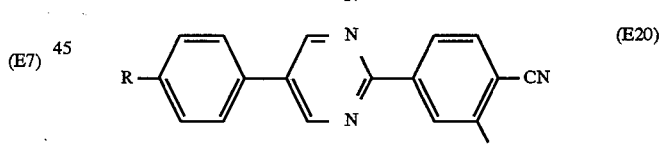
(E20)

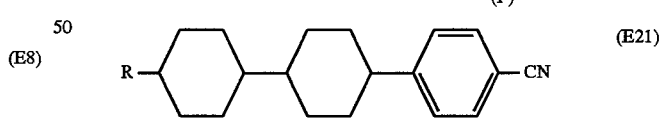
(E21)

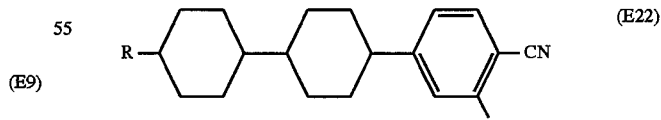
(E22)

In these formulas, R represents an alkyl group or an alkenyl group of 1 to 10 carbon atoms, and one or two methylene groups which are not adjacent to each other in the group may be replaced by oxygen atom. Further, the substituent (F) on the side position means F atom or unsubstituted H atom.

Hereinafter, the present invention will be described in more detail with reference to the Examples, but it should not be construed to be limited thereto.

In the Examples and Comparative examples, Symbols are defined as follows:

CN point: Crystal-nematic phase transition point

NI point: Nematic-isotropic liquid phase transition point

EXAMPLE 1

Preparation of (E)-2-(trans-4-(3,4,5-trifluorophenyl) cyclohexyl)-1-(trans-4-n-propylcyclohexyl)ethene (compound expressed by the formula (Ia) wherein n=3) (compound No. 1)

(i) Preparation of 3',4',5'-trifluorophenylcyclohexene-4-one-ethylene ketal (compound expressed by the formula (2) wherein X=F)

64.5 g of 3,4,5-trifluorobromobenzene in 250 ml of tetrahydrofuran (abbreviated to THF) was added dropwise in a 2 l capacity three-necked flask containing 8.0 g of magnesium and 30 ml of THF under nitrogen stream, while keeping the temperature at 50° C. Then, the reaction solution was stirred for one hour and added dropwise with a 200 ml of THF solution of 46.8 g of 1,4-cyclohexanedione-monoethylene ketal while keeping the temperature at 40° C. Further, the reaction solution was stirred for 10 hours and added with a saturated aqueous solution of ammonium chloride under ice cooling. This mixture was extracted with 500 ml of toluene. The organic layer was washed with 500 ml of water three times, dried over sodium sulfate, and concentrated.

An ion-exchange resin (Amberlist 15) in an amount of 5 g and 500 ml of toluene were added to the concentrate, followed by refluxing for 3 hours. At this time, the water flown out as an azeotrope was separated by means of a water-drain tube. The reaction solution was cooled down to 30° C., the ion-exchange resin was separated by filtration, and the resulting filtrate was concentrated to obtain 82.5 g of a crude product. The crude product was recrystallized from heptane solvent to obtain 56.1 g of the objective product. Its structure was confirmed by NMR.

(ii) Preparation of 4-(3,4,5-trifluorophenyl)cyclohexanone (compound expressed by the formula (3) wherein X=F)

The inside of a 1 l capacity eggplant type flask containing 20 g of a 5% Pd-carbon, 56.1 g of the compound obtained in (i), and 300 ml of ethanol was purged with hydrogen. The mixture was stirred at 25° C. for 8 hours to complete catalytic reduction. After separating the catalyst, it was concentrated and subjected to recrystallization from ethanol solvent to obtain 52.5 g of white crystals.

The crystals were dissolved in 200 ml of toluene and 60 g of formic acid, followed by refluxing for one hour. After allowed to cool, the reaction mixture was added with 200 ml of ethyl acetate to extract the organic layer. The extract liquid was washed with 300 ml of water, with an aqueous solution of sodium carbonate, and then with a saturated aqueous sodium chloride solution. After it was dried by adding magnesium sulfate, it was concentrated to obtain 41.5 g of a crude product. The product was recrystallized from ethanol solvent to obtain 24.5 g of the subject compound. Its structure was confirmed by NMR.

(iii) Preparation of trans-4-(3,4,5-trifluorophenyl) cyclohexanecarbaldehyde (compound expressed by the formula (4) wherein X=F)

A 1 l capacity three-necked flask containing 56.9 g of methoxymethyltriphenylphosphonium chloride and 150 ml of THF was cooled down to −10° C., followed by adding 18.5 g of potassium t-butoxide. After the reaction solution was stirred at 0° C. for one hour, a 100 ml of THF solution of 23.6 g of the compound obtained in (ii) was added dropwise. Further, the reaction solution was stirred for 4 hours and added with 300 ml of a saturated aqueous solution of ammonium chloride and 300 ml of ethyl acetate to extract. After it was washed with a saturated sodium chloride aqueous solution, it was dried by adding magnesium sulfate, concentrated, and added with 500 ml of heptane; and the deposited crystals were filtered off. The filtrate was concentrated and subjected to a column chromatography using a silica gel with heptane solvent for concentration. The concentrate was added with 150 ml of 2N hydrochloric acid and 300 ml of THF, stirred at room temperature for 8 hours, and added with 300 ml of ethyl acetate for extraction. The extract solution was washed with a saturated aqueous solution of sodium carbonate and then with a saturated aqueous solution of sodium chloride. It was dried by adding magnesium sulfate, and concentrated to obtain 26.7 g of a crude product. The product was subjected to a distillation to obtain 17.5 g of the objective compound. Its structure was confirmed by NMR.

(iv) Preparation of 2-(trans-4-(3,4,5-trifluorophenyl) cyclohexyl)-1-(trans-4-n-propylcyclohexyl)-ethene (compounds expressed by the formula (I') wherein X=F and R=n-propyl group)

A 500 ml capacity, three-necked flask containing 15.7 g of trans-4-n-propylcyclohexylmethyltriphenylphosphonium bromide and 100 ml of THF was cooled down to −50° C., followed by adding 3.5 g of potassium t-butoxide. After the reaction solution was stirred at −50° C. for one hour, a 50 ml of THF solution of 6.5 g of the compound obtained in (iii) was added dropwise, the temperature of the reaction solution was gradually raised up to 0° C. while stirring for 4 hours. The reaction system was added with 150 ml of water and 150 ml of ethyl acetate for extraction. After the separated organic layer was washed with a saturated aqueous solution of ammonium chloride and then with a saturated aqueous solution of sodium chloride, it was dried by adding magnesium sulfate and concentrated. The crude product thus obtained was added with 150 ml of heptane; the deposited crystals were filtered off; the concentrated filtrate was subjected to a silica gel column chromatography with heptane solvent; and heptane was distilled off to obtain 5.6 g of the objective product. The ratio of cis-form substance to trans-form substance was 95:5.

(v) Preparation of (E)-2-(trans-4-(3,4,5-trifluorophenyl) cyclohexyl)-1-(trans-4-n-propylcyclohexyl)ethene (compound expressed by the formula (Ia) wherein n=3)

A 100 ml capacity, three-necked flask containing 5.1 g of m- chloroperbenzoic acid, 3.0 g of potassium carbonate, and 10 ml of methylene chloride was cooled down to 10° C., followed by adding dropwise a 20 ml of methylene chloride solution of 5.6 g of the compound obtained in (iv) with stirring. After the reaction solution was stirred for 2 hours, it was added with 30 ml of a 10% aqueous solution of sodium thiosulfate and stirred for 5 minutes. After the aqueous layer was separated, the organic layer was washed with a saturated aqueous solution of sodium carbonate and then with a saturated aqueous solution of sodium chloride, and added with magnesium sulfate to dry. The solution was concentrated; the resulting crude product was subjected to a silica gel column chromatography with heptane solvent; and heptane was distilled off to obtain 5.3 g of an oily substance.

A 15 ml of toluene solution of 5.3 g of the oily substance mentioned above was added into a 100 ml capacity, three-necked flask containing 8.4 g of dibromotriphenylphosphorane and 30 ml of toluene, followed by refluxing the mixture for 6 hours. After allowed to cool, the reaction solution was subjected to a silica gel column chromatography with heptane solvent, and the solution was concentrated to obtain 7.2 g of white crystals. The crude product was recrystallized from ethanol solvent to obtain 3.4 g of white crystals. Melting point was 160° C. NMR spectra supported the objective product, (erythro-1,2-dibromo-1'-(trans-4-propylcyclohexyl)-2'-(trans-4-(2,3,4-trifluorophenyl) cyclohexyl)ethane.

Zinc in an amount of 1.5 g was added into a 100 ml capacity, three-necked flask containing 2.3 g of the dibromo substance and 20 ml of acetic acid. The reaction solution was stirred for 2 hours, poured into a 300 ml beaker containing 70 ml of water, and extracted with 100 ml of ethyl acetate. The organic layer was washed with a saturated aqueous solution of sodium carbonate and then with a saturated aqueous solution of sodium chloride, dried by adding magnesium sulfate, and concentrated to obtain 2.1 g of a crude product. The product was recrystallized from ethanol solvent and dried to obtain 0.7 g of the objective product. CN point was 51° C. and NI point was 101° C.

The following compounds are obtained according to the process mentioned above:

(E) -2-(trans-4-(3,4,5-trifluorophenyl)cyclohexyl)-1-(trans-4-methylcyclohexyl)ethene (No. 2)

(E)-2-(trans-4-(3,4,5-trifluorophenyl)cyclohexyl)-1-(trans-4-ethylcyclohexyl)ethene (No. 3) CI point: 78.6° C.

(E)-2-(trans-4-(3,4,5-trifluorophenyl)cyclohexyl)-1-(trans-4-n-butylcyclohexyl)ethene (No. 4) CN point: 52.0° C., NI point: 101.8° C.

(E)-2-(trans-4-(3,4,5-trifluorophenyl)cyclohexyl)-1-(trans-4-n-pentylcyclohexyl)ethene (No. 5) CN point: 50.7° C. NI point: 111.7° C.

(E)-2-(trans-4-(3,4,5-trifluorophenyl)cyclohexyl)-1-(trans-4-n-hexylcyclohexyl)ethene (No. 6)

(E)-2-(trans-4-(3,4,5-trifluorophenyl)cyclohexyl)-1-(trans-4-n-heptylcyclohexyl)ethene (No. 7 )

(E)-2-(trans-4-(3,4,5-trifluorophenyl)cyclohexyl)-1-(trans-4-n-octylcyclohexyl)ethene (No. 8)

(E)-2-(trans-4-(3,4,5-trifluorophenyl)cyclohexyl)-1-(trans-4-n-nonylcyclohexyl)ethene (No. 9)

(E)-2-(trans-4-(3,4,5-trifluorophenyl)cyclohexyl)-1-(trans-4-n-decylcyclohexyl)ethene (No. 10)

EXAMPLE 2

Preparation of (E)-2-(trans-4-(3,5-difluoro-4-trifluoromethylphenyl)cyclohexyl)-1-(trans-4-n-propylcyclohexyl)ethene (compound expressed by the formula (Ib) wherein n=3) (No. 11)

(i) Preparation of 3',5'-difluoro-4'-trifluoromethylphenylcyclohexen-4-one-ethylene ketal (compound expressed by the formula (2) wherein X=trifluoromethyl)

79.7 g of 3,5-difluoro-4-trifluoromethylbromobenzene in 250 ml THF solution was added dropwise into a 2 capacity, three-necked flask containing 8.0 g of magnesium and 30 ml of THF under nitrogen stream, while keeping the temperature at 50° C. Subsequently, the reaction solution was stirred for one hour and added dropwise with a 200 ml of THF solution of 46.8 g of 1,4-cyclohexanedione-monoethylene ketal while keeping the temperature at 40° C. Further, the reaction solution was stirred at room temperature for 10 hours and added with a saturated aqueous solution of ammonium chloride under ice cooling. The mixture was extracted with 500 ml of toluene. The organic layer was washed with 500 ml of water three times, dried over sodium sulfate, and concentrated.

An ion-exchange resin (Amberlist 15) in an amount of 5 g and 500 ml of toluene were added to the organic layer, followed by refluxing for 3 hours. At this time, the water flown out as azeotrope was separated by means of a water drain pipe. After the reaction solution was cooled down to 30° C., the ion-exchange resin was filtered off, and the filtrate was concentrated to obtain 101.5 g of a crude product. The crude product was recrystallized from heptane solvent to obtain 69.1 g of the objective product. Its structure was confirmed by NMR.

(ii) Preparation of 4-(3,5-difluoro-4-trifluoromethylphenyl)cyclohexanone (compound expressed by the formula (3) wherein X=trifluoromethyl)

A 1 l capacity, eggplant type flask containing 20 g of 5% Pd-carbon, 69.1 g of the compound obtained in (i), and 300 ml of ethanol was purged with hydrogen. The mixture was stirred at 25° C. for 8 hours to complete catalytic reduction. After the catalyst was separated, it was concentrated and recrystallized from ethanol solvent to obtain 64.5 g of white crystals.

The crystals were dissolved in 200 ml of toluene and 60 g of formic acid, followed by refluxing the solution for one hour. After allowed to cool down, the reaction mixture was added with 200 ml of ethyl acetate to extract the organic layer, and the extract liquid was washed with 300 ml of water and sucessively with an aqueous solution of sodium carbonate and then with a saturated aqueous solution of sodium chloride. It was added with magnesium sulfate to dry and concentrated to obtain 49.8 g of a crude product. The product was recrystallized from ethanol solvent to obtain 29.4 g of the subject compound. Its structure was confirmed by NMR.

(iii) Preparation of trans-4-(3,5-difluoro-4-trifluoromethylphenyl)cyclohexanecarbaldehyde (compound expressed by the formula (4) wherein X=trifluoromethyl)

A 1 l capacity, three-necked flask containing 57.1 g of methoxymethyltriphenylphosphonium chloride and 150 ml of THF was cooled down to −10° C., followed by adding 18.9 g of potassium t-butoxide. After the reaction solution was stirred at 0° C. for one hour, 100 ml of a THF solution of 29.4 g of the compound obtained in (ii) was added dropwise. Further, the reaction solution was stirred for 4 hours and added with 300 ml of a saturated aqueous solution of ammonium chloride and 300 ml of ethyl acetate to extract. The extract solution was washed with a saturated aqueous solution of sodium chloride, dried by adding magnesium sulfate, concentrated, and added with 500 ml of heptane, and deposited crystals were filtered off. The filtrate was subjected to a column chromatography with heptane solvent by using a silica gel again to concentrate. The concentrate was added with 150 ml of 2N hydrochloric acid and 300 ml of THF, stirred at room temperature for 8 hours, and added with 300 ml of ethyl acetate to extract, and the extract liquid was washed with a saturated aqueous solution of sodium carbonate and then with a saturated aqueous solution of sodium chloride. It was dried by adding magnesium sulfate and concentrated to obtain 31.9 g of a crude product. The crude product was subjected to a distillation to obtain 20.5 g of the objective compound. Its structure was confirmed by NMR.

(iv) Preparation of 2-(trans-4-(3,5-difluoro-4-trifluoromethylphenyl)cyclohexyl)-1-(trans-4-n-propylcyclohexyl)ethene (compound expressed by the formula (I') wherein X=trifluoromethyl and R=n-propyl group)

A 500 ml capacity, three-necked flask containing 15.7 g of trans-4-n-propylcyclohexylmethyltriphenylphosphonium bromide and 100 ml of THF was cooled down to −50° C., followed by adding 3.5 g of potassium-t-butoxide. After the reaction solution was stirred at −50° C. for one hour, 50 ml of THF solution of 7.9 g of the compound obtained in (iii) was added dropwise. The temperature of the reaction solution was gradually raised up to 0° C. while stirring for 4 hours. Water in amount of 150 ml and 150 ml of ethyl acetate were added to the reaction system for extraction, and the organic layer was washed with a saturated aqueous solution of ammonium chloride and then with a saturated aqueous solution of sodium chloride, added with magnesium sulfate to dry, and then concentrated. The crude product was added with 150 ml of heptane, deposited crystals were filtered off, and the concentrated filtrate was subjected to a column chromatography by using a silica gel column with heptane solvent, and heptane was distilled off to obtain 6.7 g of the objective compound. The ratio of cis-form substance to trans-form substance was 95:5.

(v) Preparation of (E)-2-(trans-4-(3,5-difluoro-4-trifluoromethylphenyl)cyclohexyl)-1-(trans-4-n-propylcyclohexyl)ethene (compound expressed by the formula (Ib) wherein n=3)

A 100 ml capacity, three-necked flask containing 5.1 g of metachloroperbenzoic acid, 2.9 g of potassium carbonate, and 10 ml of methylene chloride was cooled down to 10° C., and added dropwise with 20 ml of methylene chloride solution of 6.7 g of the compound obtained in (iv) with stirring. After it was stirred for 2 hours, the reaction solution was added with 30 ml of a 10% aqueous solution of sodium thiosulfate, and stirred for 5 minutes. After separating the water layer, the organic layer was washed with a saturated aqueous solution of sodium carbonate and then with a saturated aqueous solution of sodium chloride, and dried by adding magnesium sulfate. After the solution was concentrated, the resulting crude product was subjected to a column chromatography using a silica gel with heptane solvent and heptane was distilled off to obtain 6.4 g of an oily substance.

A 15 ml of toluene solution of 6.4 g of the oily substance mentioned above was added into a 100 ml capacity, three-necked flask containing 8.5 g of dibromotriphenylphosphorane and 30 ml of toluene, followed by refluxing the mixture for 6 hours. After allowed to cool, the reaction solution was subjected to a column chromatography using a silica gel with heptane solvent to concentrate the elute to obtain 8.6 g of white crystals. The curde product was recrystallized from ethanol to obtain 3.7 g of white crystals. The NMR spectra thereof supported the objective product, (erythro-1,2-dibromo-1'-(trans-4-propylcyclohexyl)-2'-(trans-4-(3,5-difluoro-4-trifluoromethylphenyl)cyclohexyl)ethane).

Zinc in an amount of 1.5 g was added into a 100 ml capacity, three-necked flask containing 2.8 g of the bromine substance and 20 ml of acetic acid. After the reaction solution was stirred for 2 hours, it was poured into a 300 ml capacity beaker containing 70 ml of water, and then extracted with 100 ml of ethyl acetate. The organic layer was washed with a saturated aqueous solution of sodium carbonate and then with a saturated aqueous solution of sodium chloride, dried by adding magnesium sulfate, and then concentrated to obtain 2.5 g of a crude product. The product was recrystallized from ethanol solvent to obtain 0.8 g of the objective product. It exhibited a CN point of 53.2° C. and an NI point of 118.9° C.

The following compounds are obtained according to the process mentioned above:

(E)-2-(trans-4-(3,5-difluoro-4-trifluoromethylphenyl)-cyclohexyl)-1-(trans-4-methylcyclohexyl)ethene (No. 12)

(E)-2-(trans-4-(3,5-difluoro-4-trifluoromethylphenyl)-cyclohexyl)-1-(trans-4-ethylcyclohexyl)ethene (No. 13)

(E)-2-(trans-4-(3,5-difluoro-4-trifluoromethylphenyl)-cyclohexyl)-1-(trans-4-n-butylcyclohexyl)ethene (No. 14)

(E)-2-(trans-4-(3,5-difluoro-4-trifluoromethylphenyl)-cyclohexyl)-1-(trans-4-n-pentylcyclohexyl)ethene (No.15)

(E)-2-(trans-4-(3,5-difluoro-4-trifluoromethylphenyl)-cyclohexyl)-1-(trans-4-n-hexylcyclohexyl)ethene (No. 16)

(E)-2-(trans-4-(3,5-difluoro-4-trifluoromethylphenyl)-cyclohexyl)-1-(trans-4-n-heptylcyclohexyl)ethene (No.17)

(E)-2-(trans-4-(3,5-difluoro-4-trifluoromethylphenyl)-cyclohexyl)-1-(trans-4-n-octylcyclohexyl)ethene (No.18)

(E)-2-(trans-4-(3,5-difluoro-4-trifluoromethylphenyl)-cyclohexyl)-1-(trans-4-n-nonylcyclohexyl)ethene (No.19)

(E)-2-(trans-4-(3,5-difluoro-4-trifluoromethylphenyl)-cyclohexyl)-1-(trans-4-n-decylcyclohexyl)ethene (No.20)

EXAMPLE 3

A liquid crystal composition A consisting of

| | |
|---|---|
| 4-(trans-4-propylcyclohexyl)benzonitrile | 30 parts by weight |
| 4-(trans-4-pentylcyclohexyl)benzonitrile | 40 parts by weight, and |
| 4-(trans-4-heptylcyclohexyl)benzonitrile | 30 parts by weight | exhibited an NI point of 52.3° C., a Δε of 10.7, a Δn of 0.119, and a viscosity at 20° C. of 22 cP. A liquid crystal composition obtained by adding 15 parts by weight of a compound of (E)-2-(trans-4-(3,4,5-trifluorophenyl)cyclohexyl)-1-(trans-4-n-propylcyclohexyl)ethene to 85 parts by weight of the liquid crystal composition A exhibited an NI point of 53.2° C., a Δε of 10.8, a Δn of 0.119, and a viscosity at 20° C. of 25.0 cP. Further, even when the composition was allowed to stand in a freezer at −20° C. for 20 days, no crystal deposited.

As seen from the above results, the compound of the present invention can raise the NI point and suppress the increase of viscosity to the utmost; thus it is seen that the compound has a superior compatibility at low temperatures.

Comparative example

In place of (E)-2-(trans-4-(3,4,5-trifluorophenyl) cyclohexyl)-1-(trans-4-n-propylcyclohexyl)ethene in Example 3, compounds (A) and (B) expressed by the following formulas were respectively added, to prepare liquid crystal compositions A and B, followed by the examination of their characteristics in the same manner as in Example 3.

Compound (A)

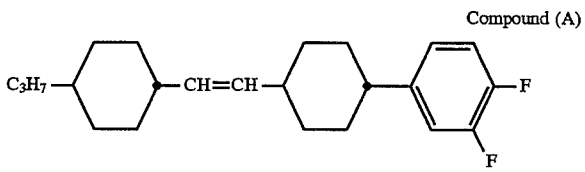

Compound (B)

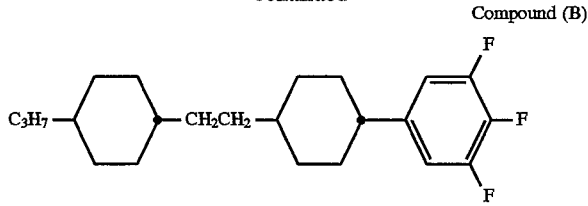

The results are shown in Table 1 together with those of Example 3:

TABLE 1

| Composition | NI point (°C.) | Δε | Δn | Viscosity (cP) | Compatibility at low temperature |
|---|---|---|---|---|---|
| Composition A | 58.9 | 9.6 | 0.114 | 22.5 | o |
| Composition B | 55.1 | 10.5 | 0.115 | 25.2 | Δ |
| Example 3 | 55.2 | 10.8 | 0.119 | 25.0 | o |

The symbol o in the column of compatibility at low temperatures means that smectic phase was not deposited and the symbol Δ therein means that smectic phase appeared.

EXAMPLE 4

A liquid crystal composition consisting of the following compounds was prepared:

| | |
|---|---|
| (E)-2-(trans-4-(3,4,5-trifluorophenyl)cyclohexyl)-1-(trans-4-ethylcyclohexyl)ethene | 8% by weight |
| (E)-2-(trans-4-(3,4,5-trifluorophenyl)cyclohexyl)-1-(trans-4-propylcyclohexyl)ethene | 9% by weight |
| (E)-2-(trans-4-(3,4,5-trifluorophenyl)cyclohexyl)-1-(trans-4-pentylcyclohexyl)ethene | 9% by weight |
| 5-pentyl-2-(3,4-difluorophenyl)pyrimidine | 11% by weight |
| 4-(trans-4-heptylcyclohexyl)-1,2-difluorobenzene | 5% by weight |
| 4-(trans-4-(trans-4-ethylcyclohexyl)cyclohexyl)-1,2-difluorobenzene | 5% by weight |
| 4-(trans-4-(trans-4-propylcyclohexyl)cyclohexyl)-1,2-difluorobenzene | 5% by weight |
| 4-(trans-4-(trans-4-pentylcyclohexyl)cyclohexyl)-1,2-difluorobenzene | 5% by weight |
| 3',4'-difluoro-4-(trans-4-ethylcyclohexyl)biphenyl | 5% by weight |
| 3',4'-difluoro-4-(trans-4-propylcyclohexyl)biphenyl | 5% by weight |
| 3',4'-difluoro-4-(trans-4-pentylcyclohexyl)biphenyl | 10% by weight |
| 4-ethyl-4'-methoxytolan | 7% by weight |
| 4-(trans-4-propylcyclohexyl)-2-fluoro-4'-ethyltolan | 6% by weight |
| 4-(trans-4-propylcyclohexyl)-2-fluoro-4'-propyltolan | 5% by weight |
| 4-(trans-4-propylcyclohexyl)-2-fluoro-4'-butyltolan | 5% by weight |

The physical properties of the composition were determined to find that NI point: 77.1° C., Δε: 5.7, Δn: 0.132, viscosity at 20° C., ($\eta_{20}$): 25.5 cP and Vth: 1.84 V.

EXAMPLE 5

A liquid crystal composition consisting of the following compounds was prepared:

| | |
|---|---|
| (E)-2-(trans-4-(3,4,5-trifluorophenyl)cyclohexyl)-1-(trans-4-propylcyclohexyl)ethene | 10% by weight |
| (E)-2-(trans-4-(3,4,5-trifluorophenyl)cyclohexyl)-1-(trans-4-pentylcyclohexyl)ethene | 10% by weight |
| 2-(trans-4-(3,4,5-trifluorophenyl)cyclohexyl)-1-(trans-4-ethylcyclohexyl)ethane | 8% by weight |
| 2-(trans-4-(3,4,5-trifluorophenyl)cyclohexyl)-1-(trans-4-butylcyclohexyl)ethane | 8% by weight |
| 2-(trans-4-(3,4,5-trifluorophenyl)cyclohexyl)-1-(trans-4-pentylcyclohexyl)ethane | 8% by weight |
| 4-(trans-4-(trans-4-ethylcyclohexyl)cyclohexyl)-1,2-difluorobenzene | 4% by weight |
| 4-(trans-4-(trans-4-propylcyclohexyl)cyclohexyl)-1,2-difluorobenzene | 4% by weight |
| 4-(trans-4-(trans-4-pentylcyclohexyl)cyclohexyl)-1,2-difluorobenzene | 4% by weight |
| trans-4-(trans-4-(3,4,5-trifluorophenyl)cyclohexyl)-1-propylcyclohexane | 7% by weight |
| trans-4-(trans-4-(3,4,5-trifluorophenyl)cyclohexyl)-1-butylcyclohexane | 3% by weight |
| 2-(trans-4-(trans-4-propylcyclohexyl)cyclohexyl)-1-(3,4,5-trifluorophenyl)ethane | 13% by weight |
| 2-(trans-4-(trans-4-pentylcyclohexyl)cyclohexyl)-1-(3,4,5-trifluorophenyl)ethane | 10% by weight |
| 4'-(trans-4-propylcyclohexyl)-3,4,5-trifluorobiphenyl | 6% by weight |
| 4'-(trans-4-pentylcyclohexyl)-3,4,5-trifluorobiphenyl | 5% by weight |

The physical properties of the composition were determined to find that NI point: 88.1° C., Δε: 7.9, Δn: 0.0814, $\eta_{20}$: 27.5 cP, and Vth: 1.61 V.

EXAMPLE 6

A liquid crystal composition consisting of the following compounds was prepared:

| | |
|---|---|
| (E)-2-(trans-4-(3,4,5-trifluorophenyl)cyclohexyl)-1-(trans-4-ethylcyclohexyl)ethene | 5% by weight |
| (E)-2-(trans-4-(3,4,5-trifluorophenyl)cyclohexyl)-1-(trans-4-propylcyclohexyl)ethene | 5% by weight |
| (E)-2-(trans-4-(3,4,5-trifluorophenyl)cyclohexyl)-1-(trans-4-pentylcyclohexyl)ethene | 5% by weight |
| 4-(trans-4-heptylcyclohexyl)-1,2-difluorobenzene | 11% by weight |
| trans-4-(trans-4-propylcyclohexyl)-1-butylcyclohexane | 12% by weight |
| 4-(trans-4-(trans-4-ethylcyclohexyl)cyclohexyl)-1,2-difluorobenzene | 4% by weight |
| 4-(trans-4-(trans-4-propylcyclohexyl)cyclohexyl)-1,2-difluorobenzene | 4% by weight |
| 4-(trans-4-(trans-4-pentylcyclohexyl)cyclohexyl)-1,2-difluorobenzene | 4% by weight |
| 3',4'-difluoro-4-(trans-4-ethylcyclohexyl)biphenyl | 8% by weight |
| 3',4'-difluoro-4-(trans-4-propylcyclohexyl)biphenyl | 8% by weight |
| 3',4'-difluoro-4-(trans-4-pentylcyclohexyl)biphenyl | 16% by weight |
| 4-(trans-4-(trans-4-propylcyclohexyl)cyclohexyl)-1-fluorobenzene | 4% by weight |
| 4-(trans-4-(trans-4-propylcyclohexyl)cyclohexyl)toluene | 7% by weight |
| 4-fluorophenyl trans-4-(trans-4-propylcyclohexyl)cyclohexanecarboxylate | 4% by weight |
| 4-fluorophenyl trans-4-(trans-4-pentylcyclohexyl)cyclohexanecarboxylate | 3% by weight |

The physical properties of the composition were determined to find that NI point: 87.6° C., Δε: 4.3, Δn: 0.0919, $\eta_{20}$: 17.7 cP and Vth: 2.22 V.

EXAMPLE 7

A liquid crystal composition consisting of the following compounds was prepared:

| | |
|---|---|
| (E)-2-(trans-4-(3,4,5-trifluorophenyl)cyclohexyl)-1-(trans-4-ethylcyclohexyl)ethene | 6% by weight |
| (E)-2-(trans-4-(3,4,5-trifluorophenyl)cyclohexyl)-1-(trans-4-propylcyclohexyl)ethene | 6% by weight |
| (E)-2-(trans-4-(3,4,5-trifluorophenyl)cyclohexyl)-1-(trans-4-pentylcyclohexyl)ethene | 6% by weight |
| trans-4-(3,4,5-trifluorophenyl)-1-heptylcyclohexane | 5% by weight |
| 4-(trans-4-propylcyclohexyl)-1-ethoxybenzene | 13% by weight |
| 4-(trans-4-(trans-4-ethylcyclohexyl)cyclohexyl)-1,2-difluorobenzene | 3% by weight |
| 4-(trans-4-(trans-4-propylcyclohexyl)cyclohexyl)-1,2-difluorobenzene | 3% by weight |
| 4-(trans-4-(trans-4-pentylcyclohexyl)cyclohexyl)-1,2-difluorobenzene | 3% by weight |
| 2-(trans-4-(3,4-difluorophenyl)cyclohexyl)-1-(trans-4-ethylcyclohexyl)ethane | 10% by weight |
| 2-(trans-4-(3,4-difluorophenyl)cyclohexyl)-1-(trans-4-propylcyclohexyl)ethane | 5% by weight |
| 2-(trans-4-(3,4-difluorophenyl)cyclohexyl)-1-(trans-4-pentylcyclohexyl)ethane | 10% by weight |
| trans-4-(trans-4-(3,4,5-trifluorophenyl)cyclohexyl)-1-ethylcyclohexane | 6% by weight |
| trans-4-(trans-4-(3,4,5-trifluorophenyl)cyclohexyl)-1-propylcyclohexane | 7% by weight |
| trans-4-(trans-4-(3,4,5-trifluorophenyl)cyclohexyl)-1-butylcyclohexane | 4% by weight |
| trans-4-(trans-4-(3,4,5-trifluorophenyl)cyclohexyl)-1-pentylcyclohexane | 4% by weight |
| 4-(trans-4-(trans-4-propylcyclohexyl)cyclohexyl)-1-fluorobenzene | 4% by weight |
| 4-(trans-4-(trans-4-propylcyclohexyl)cyclohexyl)-toluene | 5% by weight |

The physical properties of the composition were determined to find that NI point: 79.6° C., $\Delta\epsilon$: 4.9, $\Delta n$: 0.0762, $\eta_{20}$: 20.7 cP, and Vth: 1.93 V.

EXAMPLE 8

A liquid crystal composition consisting of the following compounds was prepared:

| | |
|---|---|
| (E)-2-(trans-4-(3,4,5-trifluorophenyl)cyclohexyl)-1-(trans-4-ethylcyclohexyl)ethene | 10% by weight |
| (E)-2-(trans-4-(3,4,5-trifluorophenyl)cyclohexyl)-1-(trans-4-propylcyclohexyl)ethene | 10% by weight |
| (E)-2-(trans-4-(3,4,5-trifluorophenyl)cyclohexyl)-1-(trans-4-pentylcyclohexyl)ethene | 10% by weight |
| 5-pentyl-2-(3,4-difluorophenyl)pyrimidine | 10% by weight |
| 4-(trans-4-propylcyclohexyl)benzonitrile | 10% by weight |
| trans-4-(trans-4-methoxymethylcyclohexyl)-1-propylcyclohexane | 5% by weight |
| 4-fluorophenyl trans-4-(trans-4-propylcyclohexyl)cyclohexanecarboxylate | 6% by weight |
| 4-fluorophenyl trans-4-(trans-4-pentylcyclohexyl)cyclohexanecarboxylate | 6% by weight |
| 4-(trans-4-(trans-4-ethylcyclohexyl)cyclohexyl)-1,2-difluorobenzene | 5% by weight |
| 4-(trans-4-(trans-4-propylcyclohexyl)cyclohexyl)-1,2-difluorobenzene | 5% by weight |
| 4-(trans-4-(trans-4-pentylcyclohexyl)cyclohexyl)-1,2-difluorobenzene | 5% by weight |
| 4-(trans-4-(trans-4-propylcyclohexyl)cyclohexyl)-anisole | 4% by weight |
| 4-(trans-4-(trans-4-propylcyclohexyl)cyclohexyl)-toluene | 6% by weight |
| 5-ethyl-2-(4-(trans-4-propylcyclohexyl)phenyl)-pyrimidine | 4% by weight |
| 5-propyl-2-(4-trans-4-propylcyclohexyl)phenyl)-pyrimidine | 4% by weight |

The physical properties of the composition were determined to find that NI point: 95.2° C., $\Delta\epsilon$: 7.4, $\Delta n$: 0.0978, $\eta_{20}$: 22.6 cP, and Vth: 1.91 V.

EXAMPLE 9

A liquid crystal composition consisting of the following compounds was prepared:

| | |
|---|---|
| (E)-2-(trans-4-(3,4,5-trifluorophenyl)cyclohexyl)-1-(trans-4-ethylcyclohexyl)ethene | 6% by weight |
| (E)-2-(trans-4-(3,4,5-trifluorophenyl)cyclohexyl)-1-(trans-4-propylcyclohexyl)ethene | 6% by weight |
| (E)-2-(trans-4-(3,4,5-trifluorophenyl)cyclohexyl)-1-(trans-4-pentylcyclohexyl)ethene | 6% by weight |
| 4-(trans-4-ethylcyclohexyl)benzonitrile | 12% by weight |
| 4-(trans-4-propylcyclohexyl)benzonitrile | 22% by weight |
| 4-(trans-4-pentylcyclohexyl)benzonitrile | 6% by weight |
| 4-(2-(trans-4-propylcyclohexyl)ethyl)-4'-ethyl-tolan | 4% by weight |
| 4-(2-(trans-4-propylcyclohexyl)ethyl)-4'-propyl-tolan | 4% by weight |
| 4-(2-(trans-4-propylcyclohexyl)ethyl-4'-butyl-tolan | 4% by weight |
| 3',4'-difluoro-4-(trans-4-ethylcyclohexyl)biphenyl | 3% by weight |
| 3',4'-difluoro-4-(trans-4-propylcyclohexyl)-biphenyl | 3% by weight |
| 3',4'-difluoro-4-(trans-4-pentylcyclohexyl)-biphenyl | 6% by weight |
| 4-(trans-4-propylcyclohexyl)-2-fluoro-4'-ethyltolan | 6% by weight |
| 4-(trans-4-propylcyclohexyl)-2-fluoro-4'-propyltolan | 6% by weight |
| 4-(trans-4-propylcyclohexyl)-2-fluoro-4'-butyltolan | 6% by weight |

The physical properties of the composition were determined to find that NI point: 87.6° C., $\Delta\epsilon$: 8.5, $\Delta n$: 0.1498, $\eta_{20}$: 25.7 cP, and Vth: 1.78 V.

EXAMPLE 10

A liquid crystal composition consisting of the following compounds was prepared:

| | |
|---|---|
| (E)-2-(trans-4-(3,4,5-trifluorophenyl)cyclohexyl)-1-(trans-4-ethylcyclohexyl)ethene | 4% by weight |
| (E)-2-(trans-4-(3,4,5-trifluorophenyl)cyclohexyl)-1-(trans-4-propylcyclohexyl)ethene | 4% by weight |
| (E)-2-(trans-4-(3,4,5-trifluorophenyl)cyclohexyl)-1-(trans-4-pentylcyclohexyl)ethene | 8% by weight |
| 5-propyl-2-(3,4-difluorophenyl)pyrimidine | 12% by weight |
| 4-ethyl-4'-methoxytolan | 12% by weight |
| 4-fluorophenyl trans-4-pentylcyclohexane-carboxylate | 9% by weight |
| 4-fluorophenyl trans-4-heptylcyclohexane-carboxylate | 9% by weight |
| 4-fluorophenyl trans-4-(trans-4-propylcyclohexyl)cyclohexanecarboxylate | 3% by weight |
| 4-fluorophenyl trans-4-(trans-4-pentylcyclohexyl)cyclohexanecarboxylate | 3% by weight |
| 3',4'-difluoro-4-(trans-4-ethylcyclohexyl)biphenyl | 3% by weight |
| 3',4'-difluoro-4-(trans-4-propylcyclohexyl)-biphenyl | 3% by weight |
| 3',4'-difluoro-4-(trans-4-pentylcyclohexyl)-biphenyl | 6% by weight |
| 5-propyl-2-(4'-fluorobiphenyl-4-yl)pyrimidine | 8% by weight |
| 5-butyl-2-(4'-fluorobiphenyl-4-yl)pyrimidine | 8% by weight |
| 5-pentyl-2-(4'-fluorobiphenyl-4-yl)pyrimidine | 8% by weight |

The physical properties of the composition were determined to find that NI point: 72.2° C., $\Delta\epsilon$: 7.6, $\Delta n$: 0.1572, $\eta_{20}$: 30.3 cP, and Vth: 1.74 V.

EXAMPLE 11

A liquid crystal composition consisting of the following compounds was prepared:

| | |
|---|---|
| (E)-2-(trans-4-(3,4,5-trifluorophenyl)cyclohexyl)-1-(trans-4-ethylcyclohexyl)ethene | 7% by weight |
| (E)-2-(trans-4-(3,4,5-trifluorophenyl)cyclohexyl)-1-(trans-4-propylcyclohexyl)ethene | 7% by weight |
| (E)-2-(trans-4-(3,4,5-trifluorophenyl)cyclohexyl)-1-(trans-4-pentylcyclohexyl)ethene | 7% by weight |
| 4-(trans-4-heptylcyclohexyl)-1,2-difluorobenzene | 10% by weight |
| 4-(trans-4-propylcyclohexyl)benzonitrile | 3% by weight |
| 4-(trans-4-pentylcyclohexyl)benzonitrile | 4% by weight |
| 4-(trans-4-heptylcyclohexyl)benzonitrile | 3% by weight |
| 4-(trans-4-propylcyclohexyl)-1-ethoxybenzene | 10% by weight |
| 4-ethyl-4'-methoxytolan | 11% by weight |
| 3',4'-difluoro-4-(trans-4-ethylcyclohexyl)biphenyl | 3% by weight |
| 3',4'-difluoro-4-(trans-4-propylcyclohexyl)biphenyl | 3% by weight |
| 3',4'-difluoro-4-(trans-4-pentylcyclohexyl)biphenyl | 6% by weight |
| 4-(trans-4-propylcyclohexyl)-2-fluoro-4'-ethyltolan | 6% by weight |
| 4-(trans-4-propylcyclohexyl)-2-fluoro-4'-propyltolan | 6% by weight |
| 4-(trans-4-propylcyclohexyl)-2-fluoro-4'-butyltolan | 6% by weight |
| 4-(2-(trans-4-propylcyclohexyl)ethyl)-4'-ethyltolan | 4% by weight |
| 4-(2-(trans-4-propylcyclohexyl)ethyl)-4'-propyltolan | 4% by weight |

The physical properties of the composition were determined to find that NI point: 81.3° C., $\Delta\epsilon$: 4.4, $\Delta n$: 0.1611, $\eta_{20}$: 23.5 cP, and Vth: 2.37 V.

EXAMPLE 12

A liquid crystal composition consisting of the following compounds was prepared:

| | |
|---|---|
| (E)-2-(trans-4-(3,4,5-trifluorophenyl)cyclohexyl)-1-(trans-4-ethylcyclohexyl)ethene | 3% by weight |
| (E)-2-(trans-4-(3,4,5-trifluorophenyl)cyclohexyl)-1-(trans-4-propylcyclohexyl)ethene | 3% by weight |
| (E)-2-(trans-4-(3,4,5-trifluorophenyl)cyclohexyl)-1-(trans-4-pentylcyclohexyl)ethene | 3% by weight |
| 4-ethyl-4'-cyanobiphenyl | 9% by weight |
| 4-butyl-4'-cyanobiphenyl | 8% by weight |
| 4-(trans-4-propylcyclohexyl)benzonitrile | 3% by weight |
| 4-(trans-pentylcyclohexyl)benzonitrile | 4% by weight |
| 4-(trans-heptylcyclohexyl)benzonitrile | 3% by weight |
| 4-(trans-methoxymethylcyclohexyl)benzonitrile | 4% by weight |
| 4-ethyl-4'-methyltolan | 2% by weight |
| 4-hexyl-4'-methyltolan | 4% by weight |
| 4,4'-dibutyltolan | 2% by weight |
| trans-4-(trans-4-methoxymethylcyclohexyl)-1-propylcyclohexane | 11% by weight |
| trans-4-(trans-4-methoxymethylcyclohexyl)-1-pentylcyclohexane | 12% by weight |
| 4-(trans-4-(trans-4-ethylcyclohexyl)cyclohexyl)benzonitrile | 3% by weight |
| 4-(trans-4-(trans-4-propylcyclohexyl)cyclohexyl)benzonitrile | 5% by weight |
| 4-(trans-4-(trans-4-propylcyclohexyl)cyclohexyl)toluene | 6% by weight |
| 5-propyl-2-(4'-fluorobiphenyl-4-yl)pyrimidine | 5% by weight |
| 5-butyl-2-(4'-fluorobiphenyl-4-yl)pyrimidine | 5% by weight |
| 5-pentyl-2-(4'-fluorobiphenyl-4-yl)pyrimidine | 5% by weight |

The physical properties of the composition were determined to find that NI point: 78.7° C., $\Delta\epsilon$: 8.8, $\Delta n$: 0.1462, $\eta_{20}$: 22.4 cP, and Vth: 1.75 V.

EXAMPLE 13

A liquid crystal composition consisting of the following compounds was prepared:

| | |
|---|---|
| (E)-2-(trans-4-(3,4,5-trifluorophenyl)cyclohexyl)-1-(trans-4-ethylcyclohexyl)ethene | 4% by weight |
| (E)-2-(trans-4-(3,4,5-trifluorophenyl)cyclohexyl)-1-(trans-4-propylcyclohexyl)ethene | 4% by weight |
| (E)-2-(trans-4-(3,4,5-trifluorophenyl)cyclohexyl)-1-(trans-4-pentylcyclohexyl)ethene | 4% by weight |
| 4-(trans-4-ethylcyclohexyl)benzonitrile | 12% by weight |
| 4-(trans-4-propylcyclohexyl)benzonitrile | 14% by weight |
| 4-(trans-4-methoxymethylcyclohexyl)benzonitrile | 12% by weight |
| 4-(trans-4-propylcyclohexyl)-2-fluorobenzonitrile | 12% by weight |
| 4-(trans-4-(trans-4-ethylcyclohexyl)cyclohexyl)-1,2-difluorobenzene | 4% by weight |
| 4-(trans-4-(trans-4-propylcyclohexyl)cyclohexyl)-1,2-difluorobenzene | 4% by weight |
| 4-(trans-4-(trans-4-pentylcyclohexyl)cyclohexyl)-1,2-difluorobenzene | 4% by weight |
| 5-propyl-2-(4'-fluorobiphenyl-4-yl)pyrimidine | 5% by weight |
| 5-butyl-2-(4'-fluorobiphenyl-4-yl)pyrimidine | 5% by weight |
| 4-(trans-4-(trans-4-ethylcyclohexyl)cyclohexyl)-2-fluorobenzonitrile | 8% by weight |
| 4-(trans-4-(trans-4-propylcyclohexyl)cyclohexyl)-2-fluorobenzonitrile | 8% by weight |

The physical properties of the composition were determined to find that NI point: 69.0° C., $\Delta\epsilon$: 13.9, $\Delta n$: 0.1224, $\eta_{20}$: 34.5 cP, and Vth: 1.24 V.

EXAMPLE 14

A liquid crystal compositions consisting of the following compounds was prepared:

| | |
|---|---|
| (E)-2-(trans-4-(3,4,5-trifluorophenyl)cyclohexyl)-1-(trans-4-ethylcyclohexyl)ethene | 7% by weight |
| (E)-2-(trans-4-(3,4,5-trifluorophenyl)cyclohexyl)-1-(trans-4-propylcyclohexyl)ethene | 7% by weight |
| (E)-2-(trans-4-(3,4,5-trifluorophenyl)cyclohexyl)-1-(trans-4-pentylcyclohexyl)ethene | 7% by weight |
| 4-(trans-4-pentylcyclohexyl)-1-fluorobenzene | 9% by weight |
| 4-(trans-4-hexylcyclohexyl)-1-fluorobenzene | 7% by weight |
| 4-(trans-4-heptylcyclohexyl)-1-fluorobenzene | 7% by weight |
| 4-(trans-4-(trans-4-ethylcyclohexyl)cyclohexyl)-1-trifluoromethyloxybenzene | 6% by weight |
| 4-(trans-4-(trans-4-propylcyclohexyl)cyclohexyl)-1-trifluoromethyloxybenzene | 9% by weight |
| 4-(trans-4-(trans-4-butylcyclohexyl)cyclohexyl)-1-trifluoromethyloxybenzene | 6% by weight |
| 4-(trans-4-(trans-4-pentylcyclohexyl)cyclohexyl)-1-trifluoromethyloxybenzene | 8% by weight |
| 3',4'-difluoro-4-(trans-4-propylcyclohexyl)biphenyl | 9% by weight |
| 2-(trans-4-(trans-4-propylcyclohexyl)cyclohexyl)-1-(4-trifluoromethyloxyphenyl)ethane | 8% by weight |
| 2-(trans-4-(trans-4-pentylcyclohexyl)cyclohexyl)-1-(4-trifluoromethyloxyphenyl)ethane | 7% by weight |
| 4'-(trans-4-propylcyclohexyl)-4-(trans-4-pentylcyclohexyl)-2-fluorobiphenyl | 3% by weight |

EXAMPLE 15

A liquid crystal compositions consisting of the following compounds was prepared:

| | |
|---|---|
| (E)-2-(trans-4-(3,4,5-trifluorophenyl)cyclohexyl)-1-(trans-4-ethylcyclohexyl)ethene | 8% by weight |

| | |
|---|---|
| (E)-2-(trans-4-(3,4,5-trifluorophenyl)cyclohexyl)-1-(trans-4-propylcyclohexyl)ethene | 8% by weight |
| (E)-2-(trans-4-(3,4,5-trifluorophenyl)cyclohexyl)-1-(trans-4-pentylcyclohexyl)ethene | 8% by weight |
| 4-(trans-4-pentylcyclohexyl)-1-fluorobenzene | 8% by weight |
| 4-(trans-4-hexylcyclohexyl)-1-fluorobenzene | 8% by weight |
| 4-(trans-4-heptylcyclohexyl)-1-fluorobenzene | 5% by weight |
| 4-(trans-4-(trans-4-ethylcyclohexyl)cyclohexyl)-1-trifluoromethyloxybenzene | 5% by weight |
| 4-(trans-4-(trans-4-propylcyclohexyl)cyclohexyl)-1-trifluoromethyloxybenzene | 7% by weight |
| 4-(trans-4-(trans-4-butylcyclohexyl)cyclohexyl)-1-trifluoromethyloxybenzene | 5% by weight |
| 4-(trans-4-(trans-4-pentylcyclohexyl)cyclohexyl)-1-trifluoromethyloxybenzene | 7% by weight |
| 3',4'-difluoro-4-(trans-4-propylcyclohexyl)biphenyl | 8% by weight |
| 3',4'-difluoro-4-(trans-4-pentylcyclohexyl)biphenyl | 7% by weight |
| 2-(trans-4-(trans-4-propylcyclohexyl)cyclohexyl)-1-(4-trifluoromethyloxyphenyl)ethane | 5% by weight |
| 2-(trans-4-(trans-4-pentylcyclohexyl)cyclohexyl)-1-(4-trifluoromethyloxyphenyl)ethane | 5% by weight |
| 4'-(trans-4-propylcyclohexyl)-4-(trans-4-propylcyclohexyl)-2-fluorobiphenyl | 2% by weight |
| 4'-(trans-4-propylcyclohexyl)-4-(trans-4-pentylcyclohexyl)-2-fluorobiphenyl | 2% by weight |
| 4'-(trans-4-pentylcyclohexyl)-4-(trans-4-pentylcyclohexyl)-2-fluorobiphenyl | 2% by weight |

EXAMPLE 16

A nematic composition consisting of the following compounds was prepared:

| | |
|---|---|
| (E)-2-(trans-4-(3,4,5-trifluorophenyl)cyclohexyl)-1-(trans-4-ethylcyclohexyl)ethene | 5% by weight |
| (E)-2-(trans-4-(3,4,5-trifluorophenyl)cyclohexyl)-1-(trans-4-propylcyclohexyl)ethene | 5% by weight |
| 4-(trans-4-ethenylcyclohexyl)benzonitrile | 11% by weight |
| 4-(trans-4-(E-3-pentenyl)cyclohexyl)benzonitrile | 10% by weight |
| 4-(trans-4-(3-butenyl)cyclohexyl)benzonitrile | 8% by weight |
| 4-(trans-4-propylcyclohexyl)benzonitrile | 3% by weight |
| 4'-ethyl-4-cyanobiphenyl | 7% by weight |
| 3-fluoro-4-cyanophenyl 4-ethylbenzoate | 2% by weight |
| 3-fluoro-4-cyanophenyl 4-propylbenzoate | 3% by weight |
| 4-(trans-4-(3-methoxypropyl)cyclohexyl)-2-fluorobenzonitrile | 3% by weight |
| 4-(trans-4-propylcyclohexyl)-1-pentyl-1-cyclohexene | 15% by weight |
| 4-butyl-4'-ethoxytolan | 3% by weight |
| 4-pentyl-4'-ethoxytolan | 3% by weight |
| 4-(trans-4-propylcyclohexyl)-4'-ethyltolan | 6% by weight |
| 3-fluoro-4-cyanophenyl 4-(trans-4-propylcyclohexyl)-benzoate | 9% by weight |
| 4-(trans-4-propylcyclohexyl)-4'-methoxymethylbiphenyl | 7% by weight |

EXAMPLE 17

A nematic composition consisting of the following compositions was prepared:

| | |
|---|---|
| (E)-2-(trans-4-(3,4,5-trifluorophenyl)cyclohexyl)-1-(trans-4-ethylcyclohexyl)ethene | 10% by weight |
| (E)-2-(trans-4-(3,4,5-trifluorophenyl)cyclohexyl)-1-(trans-4-propylcyclohexyl)ethene | 10% by weight |
| 4-(trans-4-ethylcyclohexyl)benzonitrile | 10% by weight |
| 4-(trans-4-propylcyclohexyl)benzonitrile | 13% by weight |
| 4-(trans-4-butylcyclohexyl)benzonitrile | 10% by weight |
| 4-(trans-4-pentylcyclohexyl)benzonitrile | 15% by weight |
| 2-(trans-4-(trans-4-propylcyclohexyl)cyclohexyl)-1-(4-fluorophenyl)ethane | 4% by weight |
| 2-(trans-4-(trans-4-pentylcyclohexyl)cyclohexyl)-1-(4-fluorophenyl)ethane | 4% by weight |
| 4-methyl-4'-ethoxytolan | 5% by weight |
| 4-pentyl-2',3'-difluoro-4'-ethoxytolan | 4% by weight |
| 2-(trans-4-(trans-4-propylcyclohexyl)cyclohexyl)-1-(4-methylphenyl)ethane | 5% by weight |
| 2-(trans-4-(trans-4-propylcyclohexyl)cyclohexyl-1-(4-ethylphenyl)ethane | 5% by weight |
| 2-(trans-4-(trans-4-propylcyclohexyl)cyclohexyl)-1-(4-propylphenyl)ethane | 5% by weight |

EXAMPLE 18

A liquid crystal composition consisting of the following compounds was prepared:

| | |
|---|---|
| (E)-2-(trans-4-(3,4,5-trifluorophenyl)cyclohexyl)-1-(trans-4-ethylcyclohexyl)ethene | 10% by weight |
| (E)-2-(trans-4-(3,4,5-trifluorophenyl)cyclohexyl)-1-(trans-4-butylcyclohexyl)ethene | 10% by weight |
| 4-(trans-4-propylcyclohexyl)-1-chlorobenzene | 5% by weight |
| 4-(trans-4-pentylcyclohexyl)-1-chlorobenzene | 5% by weight |
| 4-(trans-4-(trans-4-propylcyclohexyl)cyclohexyl)-1-chlorobenzene | 5% by weight |
| 4-(trans-4-(trans-4-pentylcyclohexyl)cyclohexyl)-1-chlorobenzene | 5% by weight |
| 4-(trans-4-(trans-4-ethylcyclohexyl)cyclohexyl)-1,2-difluorobenzene | 5% by weight |
| 4-(trans-4-(trans-4-propylcyclohexyl)cyclohexyl)-1,2-difluorobenzene | 5% by weight |
| 4-(trans-4-(trans-4-pentylcyclohexyl)cyclohexyl)-1,2-difluorobenzene | 5% by weight |
| 2-(trans-4-(3,4-difluorophenyl)cyclohexyl)-1-(trans-4-ethylcyclohexyl)ethane | 6% by weight |
| 2-(trans-4-(3,4-difluorophenyl)cyclohexyl)-1-(trans-4-propylcyclohexyl)ethane | 3% by weight |
| 2-(trans-4-(3,4-difluorophenyl)cyclohexyl)-1-(trans-4-pentylcyclohexyl)ethane | 6% by weight |
| 4-(trans-4-(trans-4-propylcyclohexyl)cyclohexyl)-1,2-difluorobenzene | 5% by weight |
| trans-4-(trans-4-(3,4,5-trifluorophenyl)cyclohexyl)-1-pentylcyclohexane | 5% by weight |
| 2-(trans-4-(trans-4-propylcyclohexyl)cyclohexyl)-1-(3,4,5-trifluorophenyl)ethane | 5% by weight |
| 2-(trans-4-(trans-4-pentylcyclohexyl)cyclohexyl)-1-(3,4,5-trifluorophenyl)ethane | 5% by weight |
| 4-(trans-4-(trans-4-propylcyclohexyl)cyclohexyl)-1-fluorobenzene | 5% by weight |
| 4'-fluoro-4-(trans-4-propylcyclohexyl)biphenyl | 5% by weight |

The physical properties of the composition were determined to find that NI point: 94.9° C., $\Delta\epsilon$: 5.4, $\Delta n$: 0.0860, $\eta_{20}$: 21.1 cP, and Vth: 2.10 V.

EXAMPLE 19

A liquid crystal composition consisting of the following compounds was prepared:

| | |
|---|---|
| (E)-2-(trans-4-(3,4,5-trifluorophenyl)cyclohexyl)-1-(trans-4-ethylcyclohexyl)ethene | 10% by weight |
| (E)-2-(trans-4-(3,4,5-trifluorophenyl) | 10% by weight |

-continued

| | |
|---|---|
| cyclohexyl)-1-(trans-4-butylcyclohexyl)ethene | |
| 4-(trans-4-(trans-4-propylcyclohexyl)cyclohexyl)-1-chlorobenzene | 7% by weight |
| 4-(trans-4-(trans-4-pentylcyclohexyl)cyclohexyl)-1-chlorobenzene | 8% by weight |
| 2-(trans-4-(3-fluoro-4-chlorophenyl)cyclohexyl)-1-(trans-4-propylcyclohexyl)ethane | 7% by weight |
| 2-(trans-4-(3-fluoro-4-chlorophenyl)cyclohexyl)-1-(trans-4-pentylcyclohexyl)ethane | 8% by weight |
| 4-(trans-4-(trans-4-ethylcyclohexyl)cyclohexyl)-1,2-difluorobenzene | 5% by weight |
| 4-(trans-4-(trans-4-propylcyclohexyl)cyclohexyl)-1,2-difluorobenzene | 5% by weight |
| 4-(trans-4-(trans-4-pentylcyclohexyl)cyclohexyl)-1,2-difluorobenzene | 5% by weight |
| 3',4'-difluoro-4-(trans-4-ethylcyclohexyl)biphenyl | 4% by weight |
| 3',4'-difluoro-4-(trans-4-propylcyclohexyl)biphenyl | 4% by weight |
| 3',4'-difluoro-4-(trans-4-pentylcyclohexyl)biphenyl | 8% by weight |
| 4'-(trans-4-propylcyclohexyl)-3,4,5-trifluorobiphenyl | 4% by weight |
| 4'-(trans-4-pentylcyclohexyl)-3,4,5-trifluorobiphenyl | 5% by weight |
| 2-(trans-4-(3,4,5-trifluorophenyl)cyclohexyl)-1-trans-4-propylcyclohexyl)ethane | 5% by weight |
| 2-(trans-4-(3,4,5-trifluorophenyl)cyclohexyl)-1-(trans-4-pentylcyclohexyl)ethane | 5% by weight |

The physical properties of the composition were determined to find that NI point: 113.1° C., $\Delta\epsilon$: 6.4, $\Delta$n: 0.1033, $\eta_{20}$: 27.7 cP, and Vth: 2.20 V.

INDUSTRIAL APPLICABILITY

Since the compound of the present invention has a high NI point, it can broaden the operation range of liquid crystal display elements. Further, since it has a low viscosity, it can improve the response speed of liquid crystal display elements. Still further, since it has a large positive $\Delta\epsilon$, it is possible to lower the driving voltage of liquid crystal display elements. Besides, since it is very stable to environment factors, it is possible to use the compound for various liquid crystal display elements (for example, that of active matrix mode by way of TFT).

We claim:

1. A dicylclohexylethylene derivative expressed by the following formula (I):

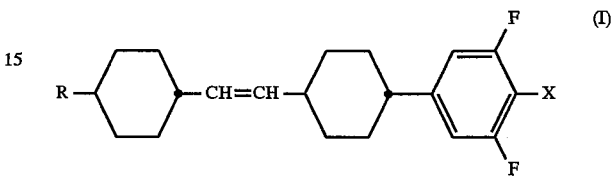

wherein R represents a linear alkyl group of 1 to 10 carbon atoms, X represents fluorine atom or trifluoromethyl group, both 1,4-cyclohexylene groups are of trans-form, and the ethenediyl group is of trans-form.

2. The dicyclohexylethylene derivative according to claim 1 wherein X represents fluorine atom.

3. The dicyclohexylethylene derivative according to claim 1 wherein X represents trifluoromethyl group.

4. A liquid crystal composition comprising at least two components at least one of which is a dicyclohexylethylene derivative according to claim 1.

* * * * *